United States Patent [19]
Soon-Shiong et al.

[11] Patent Number: 5,762,959
[45] Date of Patent: Jun. 9, 1998

[54] MICROENCAPSULATION OF CELLS

[75] Inventors: Patrick Soon-Shiong; Roswitha E. Heintz, both of Los Angeles, Calif.; Gudmund Skjak-Braek, Trondheim, Norway

[73] Assignee: Vivorx, Inc., Santa Monica, Calif.

[21] Appl. No.: 343,594

[22] PCT Filed: May 28, 1993

[86] PCT No.: PCT/US93/05122

§ 371 Date: Dec. 23, 1994

§ 102(e) Date: Dec. 23, 1994

[87] PCT Pub. No.: WO93/24112

PCT Pub. Date: Dec. 9, 1993

Related U.S. Application Data

[63] Continuation-in-part of Ser. No. 891,274, May 29, 1992, abandoned.

[51] Int. Cl.$^6$ ............... A61K 9/48; G01M 3/02
[52] U.S. Cl. ............... 424/451; 73/40; 73/64.47; 424/422; 424/423; 435/240.22
[58] Field of Search ............... 424/422, 423, 424/424, 425, 451, 488, 461; 435/178, 179, 182, 240.22; 73/12.01, 40, 64.47

[56] References Cited

U.S. PATENT DOCUMENTS

| | | | |
|---|---|---|---|
| 3,678,756 | 7/1972 | Merrill | 73/49.3 |
| 4,352,883 | 10/1982 | Lim | 435/178 |
| 4,391,909 | 7/1983 | Lim . | |
| 4,407,957 | 10/1983 | Lim | 435/178 |
| 4,663,286 | 5/1987 | Tsang et al. | 435/178 |
| 4,673,566 | 6/1987 | Goosen et al. | 424/424 |
| 4,689,293 | 8/1987 | Goosen et al. . | |
| 4,749,620 | 6/1988 | Rha et al. . | |
| 4,806,355 | 2/1989 | Goosen et al. . | |
| 4,892,538 | 1/1990 | Aebischer et al. . | |
| 4,923,645 | 5/1990 | Tsang et al. . | |
| 4,942,129 | 7/1990 | Goosen et al. . | |
| 4,950,600 | 8/1990 | Tanaka et al. | 435/178 |
| 5,073,491 | 12/1991 | Familletti . | |
| 5,084,350 | 1/1992 | Chang et al. . | |
| 5,227,298 | 7/1993 | Weber et al. | 435/178 |
| 5,232,984 | 8/1993 | Hubbell et al. . | |
| 5,429,821 | 7/1995 | Dorian et al. | 424/424 |
| 5,490,962 | 2/1996 | Cima et al. | 264/401 |

FOREIGN PATENT DOCUMENTS

| | | |
|---|---|---|
| 0 301 777 | 7/1988 | European Pat. Off. . |
| WO 85/05630 | 5/1985 | WIPO . |
| 91/09119 | 6/1991 | WIPO . |

OTHER PUBLICATIONS

Schrezenmeir et al. Long–Term Function of Porcine Islets and Single Cells Embedded in Barium–Alginate Matrix. Hormone and Metabolic Research, 25(4), pp. 204–209. (1993).

(List continued on next page.)

*Primary Examiner*—George F. Lesmes
*Assistant Examiner*—Robert H. Harrison
*Attorney, Agent, or Firm*—Stephen E. Reiter; Gray Cary Ware & Freidenrich

[57] ABSTRACT

In accordance with the present invention, it has been discovered that a major reason for the failure to achieve successful in vivo transplantation in large mammalian species has been flaws associated with the design of microcapsules taught in the prior art, flaws in the method of making such microcapsules, and a lack of tests to determine if a given microcapsule will be successful. In accordance with the present invention, a number of functional properties which must be met by a microcapsule in order to achieve successful in vivo transplantation in large animal models have been identified. These properties include (i) a mechanically stable capsule core, (ii) a mechanically strong capsule membrane (i.e., the membrane must be of sufficient strength to prevent capsule disruption), (iii) the absence of excess exposed positively-charged PLL (which leads to fibrosis), and (iv) an adequate level of diffusion of the entrapped biologically active material out of the capsule.

12 Claims, 8 Drawing Sheets

OTHER PUBLICATIONS

Horcher et al. Biocompatibility of Microbeads From Purified Alginates in Lewis–and BB–Rats. Diabetologia, Abstracts of the 29th Annual Mtg. of the EASD, p. A189, Abstract # 724.

Jacob et al. Microencapsulation of Islets Using Polyelectrolyte Complex Multilayers of Polyethylenimin and Polyacrylate. Ibid. Abstract# 725.

Lacy, Paul E. Treating Diabetes With Transplanted Cells. Scientific American, vol. 273, No. 1, pp. 50–58.(Jul. 1995).

Skjåk–Braek et al., "Inhomogeneous Polysaccharide Ionic Gels" *Carbohydrate Polymers* 10:31–54 (1994).

Freed et al., "Biodegradable Polymer Scaffolds for Tissue Engineering" *Bio/technology* 12:689–693 (1994).

MICROENCAPSULATION OF CELLS

RELATED APPLICATIONS

This application is a 371 of PCT/US93/05122, filed May 28, 1993, now abandoned, which is in turn a continuation-in-part application of U.S. patent application Ser. No. 07/891,274, filed May 29, 1992, now abandoned, the entire contents of each of which are hereby incorporated by reference herein.

This invention relates to polysaccharide gels, and to compositions and methods for encapsulating functional cores such as biologically active materials. More specifically, the present invention relates to processes for encapsulating functional materials for successful in vivo transplantation. Encapsulation compositions and methods defined by functional parameters and assays relating to the capsule core, capsule membrane and capsule biocompatibility properties have been identified which are critical for successful in vivo immunoprotectivity and for functioning in the large animal model and in discordant xenografts. Compositions of matter, articles of manufacture prepared therefrom, and methods for the use thereof are described to achieve these critical functional parameters, essential for successful in vivo application.

BACKGROUND OF THE INVENTION

Diabetes Mellitus is a life-threatening disease affecting over 100 million people worldwide. Multiple insulin injections given periodically throughout the day cannot duplicate the precise feedback of insulin secretion from the pancreas. A potential method of treatment is to extract the insulin-producing cells (islets) from a pancreas and to inject these cells into the diabetic patient, thus effecting a cure.

Microencapsulated islets as a bioartificial endocrine pancreas was described over a decade ago by Lim and Sun [Science, 210:908–910 (1980)]. By implanting islets encapsulated in calcium alginate coated with poly-L-lysine (PLL), they were able to maintain normal blood sugar levels in diabetic rats for 2–3 weeks. Due to the very gentle, simple and rapid immobilization procedure, alginate/polycation entrapment is still the most promising method for islet encapsulation and an extensive volume of literature has been devoted to this capsule. Notwithstanding the substantial body of literature and experimentation and patent art in this area, to date there have been no reports of successful long-term in vivo transplantation of encapsulated islets in large animal (canine) models by the methods of encapsulation taught in the literature or in the patent prior art. Only until viable, long term function is demonstrated in large animal models can this technology proceed to application in insulin-dependent diabetic patients.

More than a decade has passed since Lim and Sun described this technology, and successful reversal of diabetes in large mammalian models by transplantation of encapsulated islets has eluded all investigators in this field. As recently as March, 1992, in the *Journal of the American Society for Artificial Internal Organs*, Califiore reported that intraperitoneal graft of microencapsulated islet reversed diabetes in mice, but "this approach was less successful in large diabetic mammals (canines)" (*ASAIO Journal* 38:36–37 (1992). In order to overcome this deficiency in prior art capsules, Calafiore resorted to developing a vascular prosthesis, comprised of two coaxial tubes, creating a vascular chamber for encapsulated islets. This required a vascular anastomoses of the device and eliminated a major advantage of microencapsulated islets, namely, the simplicity and safety of injecting encapsulated cells, free floating, into the abdominal cavity without a major surgical procedure such as vascular anastomoses.

Thus, it is clear that difficulties in prior art capsules exist which have prevented successful long term application of alginate—PLL encapsulated islets in large animals, despite earlier success in small animal (rat and mice) trials.

Many attempts have been made to optimize or improve the performance of the capsules [see, for example, Sun et al. (1987) *Microencapsulation of cells as hormone delivery system. CRC Critical review in therapeutic drug carrier system* 4:1–12; and Goosen et al. (1984) *Optimization of microencapsulation parameters: Semipermeable microcapsules as a bioartificial pancreas. Biotechnol. Bioeng.* 27:146–150]. Despite these attempts, the methods and materials critical for successful in vivo implantation in large animals have not been elucidated.

Although some attempts have been made to optimize the performance of the capsules by improving their biocompatibility and stability [see, for example, Sun et al., (1987), supra], relatively little has been done to correlate the molecular structure and size of the main polymer component of the capsules, the alginate, to the functional properties of the resulting capsule.

An alginate—PLL capsule which contains a biologically active material or live cell(s) is taught in the prior art to comprise three main components: (i) a liquified core of calcium alginate enclosed by (ii) a polyanion/polycation complex membrane, and (iii) an outer coating of a polyanion.

The function of the polycation is to form a complex membrane which reduces and controls the permeability of the capsule. The function of the outer coating is to neutralize un-reacted PLL and thus generate a negatively-charged surface to avoid attachment of cells, such as fibroblasts, to the capsule membrane. It should also mask eventual unwanted immune responses to the polycation.

Several recent patents have attempted to perfect the materials and methods of encapsulation. Tsang et al., U.S. Pat. No. 4,663,286, discloses a method of making microcapsules by gelling the microcapsule, and then expanding the microcapsule by hydration to control the permeability of the capsule. Chang et al., U.S. Pat. No. 5,084,350, discloses microcapsules which are thereafter encapsulated in a larger matrix, which is then followed by the liquification of the microcapsules.

The prior art, however, has not yet resolved the problem of producing stable and long-lasting microcapsules in vivo. The method of making prior art microcapsules involves several steps, i.e., cells are first encapsulated in a calcium alginate gel, followed by treatment with poly-lysine to form a membrane, followed by coating the exterior with alginate, and finally, followed by a degelling of the interior alginate capsule.

Prior art capsules suffer from several problems which affect their longevity, since the requirement for liquification of the core compromises the structural integrity of the capsule. In addition, degelling is a harsh treatment to expose living cells to. Furthermore, the poly-lysine membrane, which if exposed can cause fibrosis, is not as tightly bound to the calcium alginate inner layer as it could be. Moreover, degelling of the capsule core may result in the leaching out of unbound poly-lysine or solubilized alginate, causing a fibrotic reaction to the microcapsule. These and other problems are overcome by the present invention which is described below.

SUMMARY OF THE INVENTION

There have been no reports on methods of determining whether a capsule will be successful for in vivo transplantation in large mammalian species. As used herein, the phrase "successful in vivo transplantation in large mammalian species" means the reversal of the deficient disease state for a prolonged period (at least greater than 30 days) following implantation of the encapsulated biological material. Specifically, with encapsulated insulin producing cells (islets), successful transplantation implies maintaining normal blood sugar, without the need for any exogenous insulin therapy, in a previously insulin-dependent large mammalian species (e.g., diabetic dog or Type I diabetic patient). This goal has eluded investigators for over a decade since the first description of encapsulated islets by Lim and Sun in 1980.

In accordance with the present invention, it has been discovered that a major reason for the failure to achieve successful in vivo transplantation in large mammalian species has been flaws associated with the design of the microcapsule as taught in the prior art, flaws in the method of making the capsule, and a lack of tests to determine if a capsule will be successful.

In accordance with the present invention, it has been determined that in order to achieve successful in vivo transplantation in large animal models, a number of functional properties must be met by a capsule. These properties include (i) a mechanically stable capsule core, (ii) a mechanically strong capsule membrane (i.e., the membrane must be of sufficient strength to prevent capsule disruption), (iii) the absence of excess exposed positively-charged PLL (which leads to fibrosis), and (iv) an adequate level of diffusion of the entrapped biologically active material out of the capsule.

The present invention is directed at the identification of capsule structures and compositions which enable successful long-term in vivo function following transplantation in large mammalian species and discordant xenograft models. In addition, functional assays are identified which are essential to be met in order to achieve long-term in vivo function. Through appropriate selection of capsule material in accordance with the present invention, and in a particular aspect, through control of the gelling kinetics of the material comprising the capsule, the distribution of alginate gels in the capsules can be controlled. Attention to critical factors affecting capsule core strength and capsule membrane strength result in a capsule composition not heretofore described.

Compared with prior art alginate polycation capsules, the capsules of the present invention display several improved characteristics, i.e., (i) higher mechanical and chemical stability (due to a higher gel concentration near the capsule surface, which increases the gel strength and the stability of the gel phase near the surface), (ii) higher alginate concentration near the capsule surface (causing an increased binding of polycation and a mechanically stronger membrane), and (iii) the higher gel concentration near the capsule surface provides a more effective immunobarrier (based upon a denser capsule surface (porosity) and an electrostatic barrier based on a fixed negatively-charged network).

The alginate/polycation micro capsules of the present invention (having improved mechanical and chemical stability and biocompatibility) are made by selecting capsule material (and the gelling ions therefore) according to the desired chemical structure and molecular sizes, as well as by controlling the kinetics of capsule formation. Invention capsules are preferably made from guluronic acid enriched alginate, both in the core and in the outer coating. The capsule is further characterized by having a solid alginate gel core of a defined ratio of calcium/barium alginates, with an anisotropic distribution of polymer material in the core (i.e., the concentration at the surface is much higher than in the center of the gel capsule).

Unlike prior art capsules, there is no degelling of the alginate core of invention capsules. Also, because, in a preferred embodiment, the inner core alginate is made of barium and calcium ionically cross-linked alginate, it is more stable than prior art calcium alginate, and less toxic than prior art barium alginate. Further, because of the synergistic effect of the combination of barium and calcium, there is less exchange of calcium for sodium. Also, there is an increased negative charge on the alginate core relative to prior art calcium alginate cores, which results in enhanced performance of the capsule, including increased diffusion of gene products out of the microcapsules, and, increased resistance to penetration of negatively charged antibodies into the microcapsules. The stronger binding of poly-lysine results in a stronger membrane, and also prevents leakage of poly-lysine (which in turn causes fibrosis). While barium has the stronger affinity, it is toxic in large amounts, and therefore, creates a safety hazard that is undesirable. It has, however, in accordance with the present invention, been unexpectedly found that a combination of barium and calcium, within a particular concentration range, has the benefits of high affinity without the disadvantages of a high risk of toxicity.

It has also been discovered, in accordance with the present invention, that mixing alginate compositions of high M content improve the binding of PLL in the membrane formulation step.

DETAILED DESCRIPTION OF THE INVENTION

Figure 1:
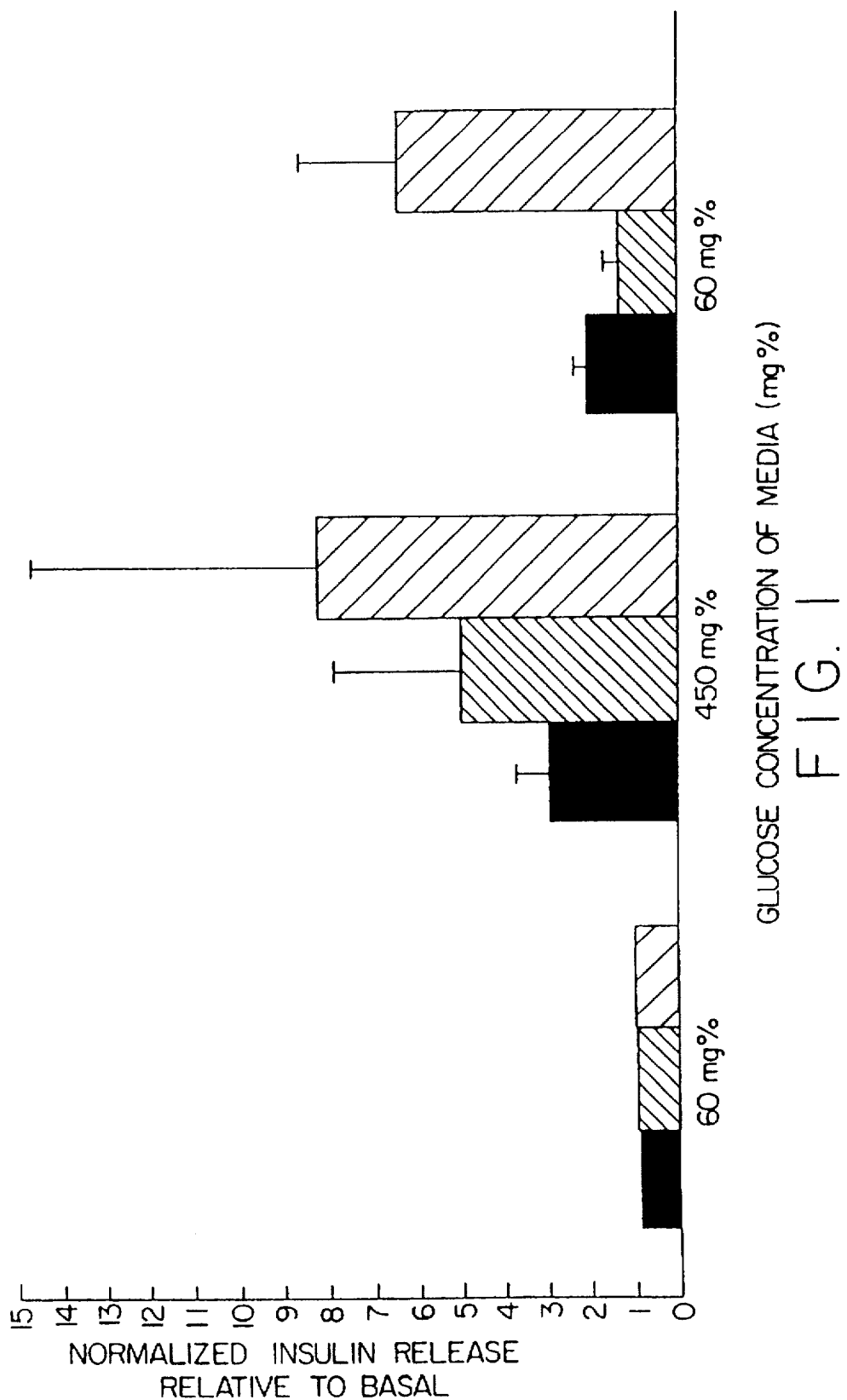
FIG. 1 presents the results of an in vitro assay (insulin secretion in response to static glucose+theophylline stimulation) demonstrating the diffusion capacity of encapsulated islets. Assays with free islets (n=2) are represented by black bars; assays with free microcapsules (n=15) are represented by densely striped bars; and assays with entrapped microcapsules (n=4) are represented by sparsely striped bars.

In accordance with the present invention, it has been discovered that a major reason for the failure to achieve successful in vivo transplantation in large mammalian species has been flaws associated with the design of the microcapsule as taught in the prior art, flaws in the method of making the capsule, and a lack of tests to determine if a capsule will be successful. The complex of factors affecting capsule properties critical for long-term in vivo success are discussed in detail herein.

Functional Properties of Capsules Critical for Successful In Vivo Transplantation A Stable Capsule Core Mechanical stability of the capsule core is critical for long-term function. In accordance with the present invention, it believed that the primary function of the core is to entrap the cells rapidly under mild conditions with the formation of a spherical bead. Secondarily, the core should serve as a template for binding of polycation, thus creating a pore structure such that the charge density on the alginate bead surface contributes to controlling the final membrane structure. Indeed, in accordance with the present invention, it has been determined that an unstable capsule core ultimately leads to disruption of the capsule membrane and graft failure. A photomicrograph (40×) of disrupted alginate microcapsules containing canine islets retrieved from the peritoneal cavity of a diabetic dog reveals that mechanical disruption of the capsule membrane has occurred. Encapsulated canine islets were transplanted into the peritoneal cavity of a diabetic recipient and successfully reversed diabetes, but only for a short period. Examination of the peritoneal cavity at time of failure demonstrated disrupted capsules, providing evidence that loss of mechanical stability plays an important role in graft failure in the large animal model.

Disruption of the capsule membrane occurs largely due to swelling of the capsule core. Swelling of the capsule core occurs in turn due to increases in osmotic pressure within the core due to an unequal distribution of unbound, mobile ($Na^+$ and $Ca^{++}$) ions. In vivo, in a large animal model, the unbound calcium within the capsule core (as well as non-gelling sodium ions) create an increased intracapsular osmotic pressure, attracting water within the core, causing capsular core swelling. A consequence of the swelling is a decrease in polymer concentration within the core, as well as increased membrane porosity, resulting ultimately in capsular failure in vivo. Thus, capsular swelling sets off a chain of events including decreased polymer concentration, an unstable capsule core, capsular disruption, exposure of poly-lysine, loss of immunoprotection of the enclosed cell, fibrosis and finally graft failure. Furthermore, the increase in porosity further adds to the loss of immunoprotection in vivo, and again ultimately graft rejection, fibrosis and graft failure.

The importance of a stable capsule core has never been recognized in the prior art. In fact, the prior art teaching of capsule formation is the opposite, i.e., to destabilize the core either by liquefying the center with sodium citrate (Lim, U.S. Pat. No. 4,352,883; Goosen, U.S. Pat. No. 4,689,293) or to swell the core with saline (Tsang, U.S. Pat. No. 4,663,286).

Since the ultimate cause of an unstable capsule core in vivo is increased osmotic pressure (as a result of unbound, mobile, free ions within the core, resulting in ingress of water and capsule swelling), stability of the capsule core can be ensured or improved by one, or a combination of two or more of the following methods:

(i) Minimizing the number of mobile ions ($Na^+$ and unbound calcium) within the gel core, by maintaining a solid gel core. This is contrary to all the teaching in prior art capsules, where the current dogma is to liquefy the gel core, which results in the opposite effect; i.e., to increase the number of mobile ions and increase the instability of the capsule core;

(ii) Utilizing an alginate composition which provides optimal mechanical strength, i.e., high guluronic acid content;

(iii) Minimizing the number of mobile ions by replacing ionic cross-linkage with covalent bonds. The current alginate gelation process involves binding of $Ca^{++}$ to lengths of G blocks. This unstable water soluble ionic bond dissociates in vivo, resulting in degelling of the core, increased number of free Ca++ ions available, capsule swelling and ultimately an unstable core. This problem can be overcome by replacing $Ca^{++}$ with a cation with higher binding affinity to alginate such as barium, or by converting the ionic bond to a covalent bond. An example of a covalently cross-linked alginate gel is that produced by photopolymerization of a polymerizable alginate, or in combination with a photopolymerizable polyethylene glycol, or a combination of ionically cross-linked alginate in combination with these polymerizable biomaterials; or (iv) Entraping the alginate-PLL-alginate microcapsule in a solid core alginate macrocapsule.

Mechanical Strength of Cansule Membrane

The polycation (Poly-lysine) forms a complex polyanion/polycation membrane with alginate, provides strength and controls the permeability of the immunoprotective alginate-PLL membrane. It has been found that it is critical that the membrane be of sufficient strength to prevent capsule disruption. The alginate-PLL membrane strength is determined by the number and strength of cross-links, which in turn is determined by the availability (concentration) of negatively-charged alginate with which the positively-charged polycation may complex. If a low concentration of alginate is available, such as in a liquefied gel core (as is taught in prior art) or a homogeneous gel core, a weak membrane ensues, resulting in in vivo capsular disruption with resultant graft failure.

Since capsule membrane strength is dependent upon the ionic interaction between polycation (PLL) and polyanion (alginate), methods of increasing capsule mechanical strength include one or more of the following:

(i) Increasing the number of available negative charges on the surface of the alginate gel core, thus allowing a higher percentage of cross-linkage with the positively charged PLL. Skjak-Braek et al. (*Carbohydrate Polymer* 10:31 (1989)) have demonstrated that alginate gels of varying degrees of anisotropy (heterogeneity) can be prepared by varying the relative concentration of gelling and non-gelling cations. They demonstrated that inhomogeneity of an alginate gel can be increased by (a) increasing the fraction of guluronic acid content and (b) decreasing the number of non-gelling cations. Since an inhomogeneous gel results in a higher polymer concentration at the surface than at the center of the gel, a higher number of negative charges would be available for membrane formation with positively-charged PLL. Thus, a stronger capsule membrane could be formed by complexing PLL with an inhomogeneous alginate gel.

An inhomogeneous gel can be formed by dissolving alginate in a solution low in ionic osmolytes, e.g., mannitol, sucrose, sorbitol, distilled water or glycerol. There are no reports in the prior art which teach the formation of such a capsule membrane. On the contrary, since prior art methods of encapsulation all teach dissolving alginate in saline, or the use of saline to swell the alginate gel, a homogenous (because of the presence of a high concentration of non-gelling cations ($Na^{++}$), rather than an inhomogeneous gel ensues. A homogenous gel results in equal or almost equal distribution of polymer concentration throughout the alginate core and eliminates the advantage of increasing negative charge density on the surface.

(ii) Capsule mechanical strength can also be increased by using an alginate composition with a higher affinity for PLL. In accordance with the present invention, it has been determined that PLL has a higher binding affinity for mannuronic acid (M), relative to the guluronic acid (G) component of alginate. Thus, to increase membrane strength, one should utilize an alginate composition with a high mannuronic acid content. However, utilizing an alginate with high M content, runs contrary to the advantages provided by alginates with high G contents (i.e., increased mechanical strength and immunological biocompatibility). To address this, several methods have been devised to take advantage of higher M alginate in the formation of capsule membrane:

(a) admixing higher M alginate (M content >50%) together with a high G alginate (G content >50%) in a solid capsule core. The high G alginate (with long G block chain lengths [NG>1=5–12]) provides the core strength, while the high M alginate (which is not bound by $Ca^{++}$) is available to be complexed with PLL. The weight ratio of high G to high M alginate in the admixture can vary widely, but is preferably 1:1.

(b) alternatively, only high G alginate is used in the capsule core, but high M alginate is used in an intermediate and outer layer of the capsule. A preferred example of such a capsule composition is described in Example 3 (with reference to the preparation of MIC-C).

(c) Yet another alternative is to provide increased negative charges within the solid alginate gel core, thus allowing increased complexation between PLL and a solid Ba/Ca alginate gel core. $Ca^{++}$ competes with PLL for binding sites within the alginate core. Tsang describes the use of saline (to swell the gel core and facilitate PLL binding), and Lim teaches complete liquefaction of the capsule (with sodium citrate) following the PLL step. These methods suffer in that the gel core is damaged by inducing instability, even though the alginate-PLL interaction is facilitated. In accordance with the present invention, a novel method of achieving increased alginate-PLL interaction without inducing instability of the core has been devised in which a Ba/Ca solid gel core is treated with a calcium chelator (such as sodium citrate, EDTA, EGTA, and the like) to remove $Ca^{++}$ ions, thereby increasing the availability of unbound negatively-charged alginate, and yet maintaining a solid, stable gel core (due to the presence of barium crosslinking). This is accomplished as described in Example 3 (with reference to the preparation of MIC-G).

The advantages and novelty of treatment of Ba/Ca solid gel core with a calcium chelator include:

(i) Despite the use of sodium citrate, the solid gel core is maintained (in contrast to prior art teaching where sodium citrate completely liquefies a calcium gel core).

(ii) Since the gel core does not dissolve after immersion of a Ba/Ca gel sphere in sodium citrate, the chelating step can be applied at any time during the encapsulation process, and thus optimize the availability of PLL to alginate. In contrast, in all prior art teachings of microcapsule formation, the sodium citrate step could only be applied after the alginate-PLL membrane was formed, i.e., after the alginate gel bead was exposed to PLL, and not before. This was necessitated by the fact that the gel bead would totally liquify if sodium citrate was applied before exposure to PLL, rendering it impossible to create a membrane with PLL thereafter. In contrast, with the solid gel core formed using the Ba/Ca combination described herein, the sodium citrate step can be applied immediately following the gel core step, thus optimizing availability of alginate to PLL within the gel core.

(iii) Increasing alginate availability within the gel core results not only in a thickened capsule membrane, but also significantly enhances biocompatibility of the membrane. In the absence of sodium citrate, it has been discovered that a capsule formulated with Ba:Ca and with excess exposure to PLL (capsule formulation J, Table 1, or with barium alone resulted in high exposure of unbound PLL on the surface of the membrane with a highly fibrogenic membrane.

(iv) By modifying the time of exposure of the gel core to sodium citrate, the availability of negative-charged alginate can be modified, and consequently, the thickness of the alginate-PLL can be fine-tuned. Evidence for this is provided by the occurrence of significantly less disruption of alginate capsules following 6 minutes of 55 mM sodium citrate exposure (75% of capsules intact after 24 hours immersion in distilled water "explosion assay") compared to alginate capsules following 1 minute sodium citrate exposure (approximately 60% intact after 24 hours of immersion in distilled water. By increasing the exposure of the gel to sodium citrate, more $Ca^{++}$ ions are chelated, increasing availability of the now negatively-charged alginate for binding to PLL, thus increasing membrane strength. The use of sodium citrate to fine-tune membrane thickness and membrane strength has not been described heretofore.

(d) Yet another alternative method to increase PLL-alginate binding is to increase the concentration of PLL, or to increase the exposure time between alginate and PLL.

(e) Yet another alternative method to increase PLL-alginate binding is to increase the negative charge density of the alginate employed, for example, by introducing sulfate groups, and the like, to the alginate.

Absence of Excess Exposed PLL

While it is critical that the capsule membrane be of sufficient strength and thickness to prevent capsular disruption, it is equally important that excess positively-charged PLL is masked or complexed by negatively-charged alginate, to prevent cellular overgrowth and fibrosis. PLL is a potent stimulator of fibroblasts and the positively-charged polycation results in cell adherence to the capsule membrane, proliferation of fibroblasts, and eventual fibrous overgrowth and graft failure.

Avoidance of exposed PLL on the surface of the capsule is critical to in vivo biocompatibility and function. In accordance with the present invention, novel methods of increasing the coating of unbound PLL with an outer alginate coat have been devised. This can be achieved in a variety of ways, such as:

(i) Applying an outer coat of alginate. By using an alginate higher in M content, increased binding of PLL occurs (and hence masking of PLL is increased).

(ii) In accordance with the present invention, it has been noted that by immersing the capsule into $CaCl_2$ (0.4% for 2 to 3 minutes) just prior to the addition of alginate, a thicker outer coat ensues due to the added gelling effect of the calcium.

(iii) By modifying the pH of the solution and of the surrounding medium in which the capsule is bathed just prior to forming the outer coat, it is possible to optimize the availability of positive charges (on PLL) and negative charges (on alginate) by taking into consideration the pKa of each component (PLL has a pKa of 10.5 and alginate has a pKa of 3.5). Thus, the optimum pH whereby charges are maximized is approximately 7. Buffer solutions can be used to maintain the pH at this level, thereby facilitating interaction of alginate and PLL. There have been no reports of utilizing pH to optimize alginate interaction.

(iv) Increased diffusion of PLL into the central core of the alginate can be accomplished by use of calcium chelator (such as sodium citrate), as described above.

(v) Exposed PLL can be masked by application of a gelled outer solid core of alginate, i.e., a macrocapsule of alginate covering a microcapsule of alginate-PLL-alginate.

Appropriate Diffusion Characteristics of the Entrapped Biological Material

In order to achieve the desired effect following in vivo transplantation, the entrapped biological material must be able to diffuse out of the capsule in a timely and adequate manner, in response to a physiological stimulus. Specifically in the case of encapsulated islets, insulin must be able to diffuse from the entrapped insulin-producing cell into the surrounding medium and be absorbed by the host's circulatory system in response to a physiological challenge of glucose. The parameters of the capsule must be designed such that this diffusion capability is met.

In accordance with the present invention, it has been discovered that alginate, by virtue of its negative charge, will increase the diffusion of negatively charged biological material (e.g., insulin) from the core of the capsule via electrostatic forces. Hence a solid core microcapsule, as well as a solid core outer macrocapsule as described above, enhances the diffusion properties of entrapped biological materials. Again this is contrary to the teachings of prior art capsules where sodium citrate is used to liquify the gel spheres with loss of alginate within the core.

Functional Assays to Determine Optimal Capsule Compositions for In Vivo Application The composition of the alginate material and the kinetics of gelation can be modified to achieve the desired properties of the capsule core and capsule membrane. Achieving the desired property of each component of this capsule in isolation, however, may fulfill the physico-chemical goals of that specific property, but may fail to provide a capsule composition that succeeds in vivo. For example, in striving to achieve a desired property for the capsule core (e.g., enhanced stability), the methods used to accomplish this outcome may run counter to a desired property for, say, a biocompatible capsule membrane. Specifically, in accordance with the present invention, it has been found that an inhomogeneous alginate gel formulated by using alginate together with Ba:Ca gelling ions in a ratio of 1:50 will adequately fulfill the criteria for a stable gel core. However, if PLL is then applied to such a gel core in a double layer (0.05% for 4 minutes, followed by 0.05% for 10 minutes; formulation J, Table 1), excess positively-charged PLL is exposed on the membrane, resulting in severe fibrosis in vivo. Hence, while such a capsule behaves adequately in vitro in terms of its physical properties (i.e., a chemically and mechanically stable capsule as evidence by in vitro dye diffusion studies), it will fail in vivo due to lack of biocompatibility.

Yet another example of the danger of satisfying individual parameters (in vitro) is demonstrated by the use of high G alginate. In accordance with the present invention, it has been shown that high G alginate provides a mechanically sound alginate gel core, and that an inhomogeneous gel provides a large negative surface area. However, if PLL is exposed to this membrane in a single layer, as taught in the prior art, a weak membrane ensues since PLL binds less well to high G than it does to high M. Thus, while the capsule core is physically stable, the membrane is weak as evidenced by the high percentage of disrupted capsules following immersion in distilled water. Evidence for this difference in strength is provided by differences demonstrated in the explosion assay (see Table 1), i.e., alginate capsules with single PLL layers (capsule formulations A, B and H, Table 1) show a lower percentage of intact capsules compared to alginate capsules with a double PLL layer (capsule formulations C, D, E and F, Table 1) following immersion in distilled water. Indeed, capsules A, B and H fail in vivo due to membrane disruption.

Thus it is clear that the ideal capsule for long-term in vivo function in small and large animal models must be formulated in such a way that it provides a balance between all of the properties critical to in vivo success. Accordingly, capsules must be formulated in a manner such that all of the following parameters, in combination, rather than in isolation, are met:

(i) stable gel core;

(ii) strong, immunoprotective capsule membrane;

(iii) biocompatible membrane without excess exposed PLL; and (iv) diffusion capacity sufficient to provide biological material to the host system in a timely manner.

In order to address these parameters in combination, in vitro assays have been devised which allow prediction of which capsules meet all the above criteria, and which capsules will succeed when implanted in a large animal. Such functional assays, which are predictive of capsule formulations which would succeed in vivo, have not been described in the art.

The in vitro assays developed in accordance with the present invention are the "Explosion Assay", the "Swelling Assay", the "Implosion Assay" (wherein various grades of membrane alteration are observed following entrapment of the microcapsule in a 1.8% high G alginate macrogel), and the "Diffusion Assay" (all of which are described in detail in Example 1).

Criteria of Functional Assays Predictive of Capsule Compositions for Successful In Vivo Transplantation In accordance with the present invention, it has been discovered that capsule compositions which result in long-term, in vivo success in large animal models meet the following functional in vitro parameters:

1. Explosion Assay: At least 5% of the original capsules remain intact following immersion in distilled water for 24 hours.
2. Implosion Assay: Not greater than 2+ implosion as defined in the implosion assay described herein.
3. Swelling Assay: No greater than 180% swelling of original capsule volume after 12 hours exposure in saline.
4. Diffusion Assay: At least 1.5× basal stimulation of the end product in vitro, following maximum stimulation.

In accordance with the present invention, it has been found that capsules which pass all of the above functional assays prove successful in vivo in large animal models. As a corollary, capsules which fail one or more of the above functional assays fail to provide long-term function in vivo. The following non-limiting examples are provided to illustrate the preparation of capsules of the invention and to demonstrate the excellent correlation between the functional assays described herein and in vivo success.

EXAMPLE 1

In vitro Assays

"Explosion Assay"

Alginate microcapsules (20 to 30 in number) are transferred to 10 cc distilled water and examined microscopically at regular intervals (2 minutes, 4 minutes, 10 minutes, 20 minutes, 30 minutes, 60 minutes, 2 hours, 4 hours, 12 hours, 24 hours) post immersion. The alginate capsules swell due to ingress of water and eventually explode. A microcapsule formulated by the Lim method exploded. In accordance with the present invention, it has been found that the percentage of capsules which swell and explode over time is a function of both (i) capsule core stability, and (ii) capsule membrane strength.

Capsules of varying compositions, as follows, have been studied:

(A) Lim capsule (low G alginate-PLL-alginate with liquification of gel core); Microcapsule A, "MIC-A"; prepared employing 1.3% sodium alginate (low G) in saline, in 1.1% $CaCl_2$ in saline; then applying an alginate-PLL membrane by crosslinking with PLL, (0.05%×10 min.); then applying an outer alginate coat (0.15%×10 min); and finally liquefying the core with sodium citrate (55 mM×6 min.).

(B) Lim capsule (high G alginate-PLL-alginate with liquification of gel core); Microcapsule B, "MIC-B"; prepared employing 1.6% sodium alginate (high G) in saline in 1% $CaCl_2$ in saline; then applying an alginate-PLL membrane with PLL (0.05%×10 min.); then applying an outer alginate coat (0.15%×10 min.); and finally liquifying the core with sodium citrate (55 mM×6 min.).

(C) Novel method: Pentalayer high G alginate (inhomogenous solid gel core-PLL-alginate (high M)-PLL-alginate (high M)); Microcapsule C, "MIC-C"; prepared employing 1.8 to 2.0% high G alginate in 5% mannitol (non-ionic) in 0.4% $CaCl_2$ (low $Ca^{++}$ content; then applying a PLL membrane (0.1%×3 min.); then applying an intermediate algnate coat using high M alginate (0.2%×10 min.); a possible variation is the use of high G alginate in this step—see MIC-E); then applying a PLL membrane (0.05%× 10 to 12 min.), thereby producing a strengthened membrane, and finally applying an outer alginate coat using high M alginate (0.2%×10 min.) a possible variation is the use of high G alginate in this step—see MIC-E).

(D) Novel method: Pentalayer (Admixture high G alginate with high M alginate inhomogeneous solid gel core-PLL-alginate-PLL-aginate); Microcapsule D, "MIC-D"; prepared employing 1.8% high G calcium alginate and 1.8% high M calcium alginate in 5% mannitol, in 0.4% $CaCl_2$ (producing an inhomogeneous gel), then applying a PLL membrane (0.1%×3 min); then applying an intermediate alginate coat using high G or high M alginate (0.2%×10 min); then applying a PLL membrane (0.05%×10 to 12 min), thereby producing a strengthened membrane, conducting a $CaCl_2$ prewash; and finally applying an outer alginate coat using high G or high Malginate (0.2%×10 min.).

(E) Novel method: Pentalayer (high G-alginate inhomogeneous solid gel-PLL-alginate (high G)-PLL-alginate (high G)); Microcapsule E, "MIC-E"; prepared employing 1.8 to 2.0% high G alginate in 5% mannitol (non-ionic) in 0.4% $CaCl_2$ (low $Ca^{++}$ content); then applying a PLL membrane (0.1%×3 min.); then applying an intermediate alginate coat using high G alginate (0.2%×10 min.); then applying a PLL membrane (0.05%×10 to 12 min.) and finally applying an outer alginate coat using high G alginate (0.2%×10 min.). ). Note that MIC-C with high M in the intermediate layer demonstrates a stronger membrane than MIC-E with high G.

(F) Novel method: Ba:Ca inhomogeneous gel core-PLL-alginate-PLL-alginate (Microcapsule F, "MIC-F"); prepared employing a high G Ca:Ba alginate core having a high negative charge on the gel surface (1.8% high G alginate (or a 1:1 mixture of high G and high M alginate) in 1:50 $BaCl_2$:$CaCl_2$ in 0.4% $CaCl_2$ in mannitol (inhomogeneous gel); then applying a PLL membrane (0.05% ×3 min.); then applying an intermediate alginate coat; using high G and/or high M alginate in various combinations (0.2%×10 min); then applying a PLL membrane (0.05%×4 min.) and finally applying an outer alginate coat; using high G and/or high M alginate in various combinations (0.2%×10 min.).

(G) Novel method: Ba:Ca inhomogeneous gel core-sodium citrate-PLL-alginate (Microcapsule G, "MIC-G"); prepared employing 1.8% high G alginate in 5% mannitol in 1:50 $BaCl_2$:$CaCl_2$ (0.4% $CaCl_2$ in mannitol; (an inhomogeneous gel having a high negative charge on the gel surface); then applying sodium citrate (55 mM×1 to 6 min.); then applying a PLL membrane (0.05 to 0.1% PLL, 3 to 6 min.); and finally applying an outer alginate coat using high M or high G alginate (0.2%×10 Min.).

(H) Novel method: Ba:Ca inhomogeneous gel core-PLL-alginate (Microcapsule H, "MIC-H"); prepared employing 1.8% high G alginate in 5% mannitol in 1:50 $BaCl_2$:$CaCl_2$ (0.4% $CaCl_2$ in mannitol); then applying a PLL membrane (0.05%×10 min.); then applying an outer alginate coat (0.2%×10 min).

(I) Novel Method: Ba:Ca inhomogeneous gel core-PLL-alginate-PLL-alginate (Microcapsule I, "MIC-I"); prepared employing a high M/high G Ca:Ba alginate core (1.8% high G alginate and 1.8% high M alginate in 1:50 $BaCl_2$:$CaCl_2$ in 0.4% $CaCl_2$ in mannitol (inhomogeneous gel); then applying a PLL membrane (0.05%×3 min.); then applying an intermediate high G/high M alginate coat (0.2%×10 min); then applying a PLL membrane (0.05%×4 min.) and finally applying an outer high G/high M alginate coat (0.2%×10 min.)

(J) Novel method: Ba:Ca inhomogeneous gel core with PLL-PLL-alginate (Microcapsule J. "MIC-J"); prepared employing 1.8% high G alginate in 5% mannitol, in 1:50 $BaCl_2:CaCl_2$, 0.4% $CaCl_2$ in mannitol then applying a PLL membrane (0.05%×4 min.); then applying a second PLL membrane (0.05%×10 min.); and finally applying an outer alginate coat using high G and/or high M alginate in various combinations (0.2%×10 min.).

The results are summarized in Table 1:

TABLE 1

| CAPSULE TYPE | CORE | ALGINATE COMPOSITION | EXPLOSION ASSAY (% Capsules Intact) | | | | | |
|---|---|---|---|---|---|---|---|---|
| | | | 4' | 10' | 20' | 30' | 60' | 24 hrs |
| A. Standard | Liquid | Low G | 100 | 0 | 0 | 0 | 0 | 0 |
| B. Standard | Liquid | High G | 100 | 76 | 76 | 76 | 76 | 5 |
| C. Novel | Solid ($Ca^{++}$) | High G | 100 | 100 | 98 | 98 | 98 | 98 |
| D. Novel | Solid ($Ca^{++}$) | High G+ High M | 69 | 50 | 45 | 42 | 39 | 18 |
| E. Novel | Solid ($Ca^{++}$) | High G | 97 | 87 | 85 | 85 | 81 | 76 |
| F. Novel | Solid (Ca:Ba) | High G | 100 | 100 | 98 | 96 | 92 | 69 |
| G. Novel | Solid (Ca:Ba) | High G | 86 | 72 | 66 | 62 | 62 | 57 |
| H. Novel | Solid (Ca:Ba) | High G | 91 | 16 | 0 | 0 | 0 | 0 |
| I. Novel | Solid (Ca:Ba) | High G+ High M | 74 | 64 | 58 | 51 | 47 | 33 |
| J. Novel | Solid (Ca:Ba) | High G | 100 | 100 | 96 | 92 | 92 | 84 |

Thus, the higher the stability of the capsule core, the greater (thicker) the capsule membrane strength, the lower number of capsules will swell and explode.

"Swelling Assay"

This is a milder variation of the explosion assay in that the capsules are immersed in 0.9% saline, and observed over time for swelling. This swelling assay is a function of the stability of the capsule core. An inhomogeneous capsule core with high mechanical strength (high G alginate) and strong ionic bonds (e.g., barium) demonstrated minimal swelling (<20% over a 12 hour period), whereas a liquified capsule core of low mechanical strength and low chemical stability composed of a high M Alginate core (Capsule Type A, Table 1) demonstrated rapid swelling during the production of the capsule (>180% of its original size) and was shown to be highly unstable when placed in vivo.

"Implosion Assay"

A strong capsule membrane implies a membrane with high PLL content and rigidity associated with such a membrane. While strength in the membrane is critical (as demonstrated by low explosion and low swelling assay above), it is important to recognize that biocompatibility is also critical for in vivo success, i.e., no excess exposed PLL on the membrane surface. In accordance with the present invention, an assay has been developed which predicts the biocompatibility or lack of biocompatibility of the PLL membrane. This assay is performed by encapsulating 30 to 40 alginate microcapsules (1 ml capsule pellet) in a 1.8% alginate macrocapsule gel. In the presence of capsules with excess PLL on the membrane (and hence not biocompatible when placed in vivo) severe indentations or in folding of the PLL membrane occurs (Grade 3+). In the face of excess PLL and a very rigid membrane, this indentation or folding of the membrane of the entrapped microcapsule can be extreme and the capsule appears to "implode" on itself. It is, therefore, possible to grade, in a functional manner, the rigidity, the thickness, and consequently the potential biocompatibility of the PLL membrane by this implosion assay. The various degrees of implosion noted with capsule compositions containing various thicknesses of PLL membranes are as follows:

| Rating | Observations |
|---|---|
| 0 = | Even surface of membrane |
| 0.5+ = | Striations noted on membrane |
| 1.0+ = | Mild indentations |
| 2.0+ = | Larger indentations but no large infolding of the membrane |
| 3.0+ = | Severe infolding (implosion) of the membrane; capsules which demonstrate 3+ are predictive of fibrosis if implanted in vivo. |

An example of the in vivo predictive value of the implosion assay is demonstrated by inspection of microcapsule MIC-J, revealing a Grade 3+ imploded alginate capsule (based on a Ba:Ca formulation and excess PLL on the surface). When this microcapsule was implanted into the peritoneal cavity of Lewis rats and retrieved after 7 days, severe fibrosis was noted, as can be expected from a capsule with excess PLL on the surface. In contrast, inspection of microcapsule MIC-A reveals an alginate capsule formed with minimum implosion, predicting that the PLL has complexed well with the surrounding alginate. This capsule was implanted into Lewis rats and, as predicted by the assays described herein, minimal overgrowth was noted on retrieval of the capsule after 7 days. While these capsules exhibit the property of biocampatibility based on the results of the implosion assay (0 to 0.5+ grade), long-term stability was poor, as predicted by the results of the explosion assay.

It is clear to anyone skilled in the art, that the capsule gel which is used to entrap the microcapsules (thereby producing a macrocapsule) can be of any gelling or polymerizable material such as alginate, agar, polymerizable PEG, etc.

Implosion results of capsule formulations A to J (as described in Table 1) are presented in Table 2:

TABLE 2

| CAPSULE TYPE | IMPLOSION ASSAY |
|---|---|
| A | 0 to 0.5+ |
| B | 0 to 0.5+ |
| C | 0 to 1+ |
| D | 0 to 1+ |
| E | 0 to 1+ |
| F | 2+ |
| G | 2+ |
| H | 2+ |
| I | 2+ |
| J | 3+ |

"Diffusion Assay"

Diffusion of the gel entrapped biological material can be assessed by an in vitro functional study whereby the entrapped cell is stimulated to release an end-product, and the rapidity as well as extent of release of this end-product, is measured.

Specifically, encapsulated islets are stimulated with glucose, and theophylline, and insulin secretion measured.

Kinetics of insulin secretion from the gel entrapped encapsulated canine islets were compared to individual microencapsulated islets or unencapsulated canine islets as follows: either free unencapsulated canine islets (controls) or encapsulated canine islets or gel entrapped encapsulated canine islets were incubated in RPMI culture medium containing a basal level of 60 mg % glucose for 60 minutes, then transferred to medium containing a stimulatory level of 450 mg % glucose and 10 mM theophylline for 60 minutes and returned to basal medium (60 mg % glucose) for an additional 60 minutes. These tests were performed in triplicate. The supernatant was collected at the end of each 60 minute period. Insulin secretion was assayed by measuring insulin concentration (μU/ml per islet equivalent count) in the supernatant, using RIA. The results are shown in FIG. 1, which shows an example of encapsulated islets ("Free MC"), demonstrating excellent release of insulin compared to basal levels. In accordance with the present invention, it has been found that a release level of 1.5 to 2× basal demonstrates diffusion capacity sufficient to provide adequate function when transplanted in vivo.

EXAMPLE 2

Capsule Formulations which Fail the Above-described Functional Parameters and which Fail In Vivo Prior Art Capsule Formulations:

Lim (U.S. Pat. No. 4,352,883; Oct. 5, 1982) described alginate formulations whereby the gel within the membrane is re-liquefied using sodium citrate (see Claim 1e, U.S. Pat. No. 4,352,883). When this formulation is tested in the explosion assay, 100% of the capsules are disrupted by 10 minutes (see Table 1), demonstrating a very unstable gel core (since it has been re-liquified) as well as a mechanically weak membrane. The implosion assay demonstrated a 0 to 1+ grade (see Table 2), predicting that the capsule is biocompatible in terms of exposed PLL on the surface.

In vivo studies confirmed the outcome predicted by these functional assays. Empty microcapsules, formulated by the method taught by Lim, demonstrated no overgrowth of intact capsules when retrieved after 7 days intraperitoneal implantation in normal Lewis rats (corroborating the results of the implosion assay). Disrupted capsules were also retrieved (confirming the results of the explosion assay. These Lim capsules failed to provide long-term immunoprotection, as demonstrated by rapid failure (within 14 days) following canine xenografts in diabetic Lewis rats. Even rat encapsulated allografts failed rapidly. Retrieval of these encapsulated islets demonstrated capsular disruption with dense fibrous overgrowth of the capsule membrane. Goosen et al. (U.S. Pat. No. 4,689,293) corroborates these findings by demonstrating that capsules formulated by the Lim method provide function for only 2 to 3 weeks in rats (see Goosen Example 3).

This weakness in the capsule core thus explains to a large extent why there have been no reports of successful encapsulated islet transplants in large animal models for over a decade since the first description of this method by Lim and Sun in 1980.

Various attempts at improving this capsule formulation have been attempted by Tsang (U.S. Pat. No. 4,663,286; May 5, 1987), by Goosen et al. (U.S. Pat. No. 4,689,293; Aug. 25, 1987), and by Goosen et al. (European Patent application Number 88306789.4). All of these attempts, however, fail to address the fundamental weakness of the alginate gel core. Tsang concentrated his efforts on improving the porosity of the capsule membrane, rather than on the strength of the capsule gel core. In fact, the gel core was rendered even more unstable by saline washings as taught by Tsang (U.S. Pat. No. 4,663,286; claim 1B). The re-liquification step (U.S. Pat. No. 4,663,286; claim 3) was continued, adding further weakness to the gel core. Similarly, Goosen et al. (U.S. Pat. No. 4,689,293) concentrated on modifying the polycation membrane, and still taught liquification of the gel core. Again, capsules formulated by this method have failed to provide in vivo function in large animal (canine) models.

In European Patent Application 88306789.4, Goosen describes multiple layers of polycation membranes, but again teaches liquifying the gel core. In fact, the goal of this method was to decrease, as opposed to increase, the concentration of the intracapsular gel core. In example 6 of the Goosen application, it is indicated that "the multiple membrane microcapsules contained about 23% less alginate than the standard microcapsules." With this decrease in polymer concentration within the gel core, a highly unstable capsule results in vivo.

Chang (U.S. Pat. No. 5,084,350; Jun. 28, 1992) describes a variation of multiple capsule membranes using PLL, but again teaches re-liquification of the gel within such membranes (see claim 1e, U.S. Pat. No. 5,084,350).

Capsule Formulation Using Barium as an Ionic Gel:

1.8% high G alginate (Protan Biopolymer, Norway) was gelled in a 1:10 ratio of $CaCl_2:BaCl_2$, resulting in a strong alginate gel core. Thereafter, 0.05% PLL was complexed with the gel sphere for 4 minutes, followed by a second coat of PLL (0.05% ×10 mins) and then by an outer layer of 0.2% high G alginate. In vitro functional parameters demonstrated the following: 4% explosion in 20 minutes (demonstrating a highly stable gel core and strong capsule membrane) and 3+ implosion (predicting fibrous overgrowth). Retrieved empty capsules implanted into the peritoneal cavity of Lewis rats demonstrated severe fibrous overgrowth after 7 days.

A modified version of the above capsule formulation was attempted using a $BaCl_2:CaCl_2$ combination (1:50 ratio) and 0.04M $CaCl_2$ as the gelling cation with 0.05% PLL for 10 minutes. A high explosion level (<5% intact after 24 hours) and low implosion assay (1+) was noted. Canine islets were encapsulated by this formulation and transplanted into a pancreatectomized, diabetic dog. Euglycemia (normalization of blood glucose below 200 mg %) was achieved, but maintained for only 2 days, after which the diabetic state recurred. Examination of the peritoneal cavity revealed microcapsules tightly adherent to the omental tissue, confirming the poor biocompatibility and poor immunoprotectivity of this formulation.

EXAMPLE 3

Capsule Formulations which Meet the Above-described Functional Parameters and Demonstrate Long-Term In Vivo Function in the Large Animal Model Inhomogeneous Gel Core with High Guluronic Acid Content and Sandwich Layer of PLL (Pentalayer Microcapsule)

The method and principles of this formulation are as follows:

(i) a solid high G alginate core provides increased mechanical strength, and improved biocompatibility (decreased cytokine stimulation);

(ii) by forming an inhomogeneous solid gel core, the capsule membrane is strengthened due to increased negative charge density available on the surface to which PLL may bind. An inhomogeneous gel core is accomplished by dissolving alginate in a liquid with low ionic osmolyte content. In this example, 1.8% high G alginate (>50% G with a block length >5) is dissolved in a 5% mannitol solution. In addition, by using a low concentration of calcium (0.05M), dissolved in 5% mannitol solution, inhomogeneity of the capsule gel core is increased;

(iii) A sandwich layer of PLL is used, i.e., following entrapment of the islet in an inhomogeneous high G alginate gel core, the capsule membrane is formed by exposure to PLL (0.1%) for 3 minutes. This is followed by application of an intermediate layer of either high M or high G alginate, which serves as a template for the second layer of PLL. By virtue of this sandwich layer of PLL-alginate-PLL, the capsule membrane is significantly strengthened. If high G alginate is used in the sandwich layer, saline washes (0.9% NaCl) for 10 minutes between each application of PLL is a necessary step.

(iv) An outermost layer of either high M or high G alginate (the pentalayer) is applied to mask or cover any unbound PLL, thereby preventing excess exposure of positively charged PLL.

For example, MIC-C is prepared as follows: 1.8% high G alginate (G content >50%, G block chain lengths >5) solid core (an inhomogeneous gel is formed by extruding the high G alginate [1.8% alginate solution in low osmolyte medium of 5% mannitol] through a droplet generator into a 0.05M $CaCl_2$, dissolved in 5% mannitol solution), followed by PLL exposure (0.1% for 3 minutes), followed by an intermediate layer of high M alginate (0.2% for 10 minutes) to facilitate PLL interaction, then, a second PLL layer (0.05% for 10 minutes), followed by an outer coat of high M alginate (0.2% for 10 minutes). In accordance with the present invention, it has been determined that this "sandwich" method provides improved capsule membrane strength, as compared to a single PLL layer (microcapsules MIC-A, MIC-B and MIC-H, Table 1). Furthermore, this double layer of high M alginate (MIC-C, Table 1) provides a stronger membrane when compared to a double layer of high G alginate (compare MIC-E, Table 1). Evidence of this is provided by the explosion assay. This is believed to be the first report of modulating PLL membrane strength by using alginates of a specific (high M) composition.

Canine islets were encapsulated using formulation MIC-C, and transplanted into spontaneous diabetic dogs. Results are discussed below.

Use of High M Alginate (>50%M):

Two variations of microcapsules of the formulation described above are accomplished by the following changes:

Variation (a) (MIC-D):

A mixture of high G (>50% G, with G block length at least >5) and high M (>50% M) alginate is used in the gel core, on the basis that PLL binds preferentially to high M alginate, thereby increasing capsule membrane strength. The presence of high G alginate provides increased mechanical strength within the capsule core. A 2% solution of high G alginate in 5% mannitol is mixed with a 1.6% solution of high M alginate (40% G). Islets are entrapped in this mixture by an inhomogeneous gel. The remaining steps are as described above for the preparation of MIC-C. The preferred ratio of the mixture of High G to High M is 1:1, but any variation or combination of ratios will suffice.

Variation (b) (MIC-E):

High G alginate (instead of high M alginate) is used in the PLL-alginate-PLL sandwich layers. The outer alginate coat is also of an alginate with a high G content. It is clear to anyone skilled in the art that variations of combinations of high G and high M alginate in the sandwich and outer layer can be used, e.g., high M in the outermost layer only, with high G alginate in the intermediate layers of PLL.

Similarly, variations in combinations of the M and G content in the capsule core relative to G and M content in the intermediate sandwich layer and outer core are possible.

Capsules of variations MIC-C, MIC-D and MIC-E were formulated, and canine islets encapsulated in this material were transplanted intraperitoneally into spontaneous diabetic dogs (results discussed below).

Use of Barium Chloride

The addition of barium chloride as a gelation cation will increase the capsule core stability since barium has a high binding affinity for alginate.

In this example, barium chloride is combined with calcium chloride, preferably in 1:50 ratio (the ratio can vary from 1:20 to 1:1000), using 0.05M calcium chloride. An inhomogeneous solid gel core is formed by using a non-ionic osmolyte in the gelling solution (5% mannitol). Following formation of the alginate gel core, the remaining steps are as described above for the preparation of MIC-C, except the concentration and duration of exposure of PLL is decreased (to prevent excess unbound PLL exposed on the surface of the membrane, 0.05%×3 mins., and 0.05%×10 mins.).

A variation of this formulation is provided by the use of sodium citrate to remove calcium ions from the solid gel core, yet maintaining the gelled state (due to the presence of barium cross-links), and thereby facilitating PLL complexation with the alginate gel core (MIC-G). Under these circumstances, only a single exposure of 0.05% PLL for 5 to 6 minutes is necessary to accomplish a very strong capsule membrane.

Thus, MIC-G is prepared by combining barium with calcium in a 1:2 to 1:1000 (preferably 1:50 to 1:100) ratio in the capsule gelation step. In this way, a solid core inhomogeneous gel is formed using both barium and calcium as ionic cross-linking cations within the alginate core. Immediately following this step, the gel spheres are immersed in sodium citrate (5 to 55 mM for 1 to 6 minutes) to remove all calcium ions. Since the barium cross-link is not disrupted by the addition of sodium citrate, the solid core gel remains intact, while availability of negatively-charged alginate is now increased (by removal of $Ca^{++}$), thus increasing PLL-alginate interaction, resulting in a stronger membrane. This is the first description of the use of a chelator to enhance alginate-PLL interaction. As can be seen in Table 1, with reference to MIC-G, a much stronger capsule was formed with the use of sodium citrate than without (compare MIC-H).

It should be apparent to anyone skilled in the art that the variations MIC-C, MIC-D, MIC-E, MIC-F, MIC-G, MIC-H and MIC-I, together with all combinations of high G or high M alginate in the sandwich layers and outer cores, can be applied using $BaCl_2:CaCl_2$ as the gelling solution, with or without the use of sodium citrate.

Canine islets were encapsulated by these techniques, and transplanted intraperitoneally into spontaneous diabetic dogs (results discussed below).

The differences between invention microcapsules MIC-C, MIC-D, MIC-E, MIC-F, MIC-G, MIC-H and MIC-I, and standard formulations in the prior art, are summarized in Table 3:

Table 3

| | Standard Capsule Formulation (Prior Art) | Novel Capsule Formulation |
|---|---|---|
| 1. Functional Parameters as a whole: Explosion Assay Implosion Assay Diffusion Assay Swelling Assay | Fail | Pass |
| 2. Solid Gel Core | Absent | Present |
| 3. Liquified Gel Core | Present | Absent |
| 4. Inhomogeneous Gel Core | Absent | Present |
| 5. Use of High G in Solid Core | Absent | Present |
| 6. Use of Admixture of High G and M in solid Core | Absent | Present |
| 7. Use of Ba:Ca combination as gelling cations | Absent | Present |
| 8. Use of High M Alginate in increasing membrane strength | Absent | Present |
| 9. Use of Pentalayer Capsule with solid core gel | Absent (Triple) (Liquid Core) | Present |
| 10. Use of Na Citrate to increase membrane strength immediately following gelation step | Absent | Present |
| 11. Successful Long-Term reversal of Diabetes in large animal models | Failed | Long-term Success |
| 12. Long-term highly discordant xenograft function with short-term cytokine suppression | Failed | Long-term success |
| 13. Increased immunoactivity due to solid core | Absent | Present |
| 14. Increased diffusion of entrapped biological end product (electrostatic discharge) | Absent | Present |

EXAMPLE 4

In Vivo Function and the large Animal Model

The formulations described above were all shown to pass the following functional parameters:

(i) explosion assay (>5% intact after 24 hours exposure to distilled water);

(ii) minimal implosion (0 to 2+ grade);

(iii) adequate diffusion (glucose stimulation index of 2× basal); and (iv) swelling (no greater than 180% of original volume over 12 hours exposure to saline).

Canine islets were encapsulated by these formulations, and transplanted intraperitoneally into spontaneous diabetic dogs (n=6). Three dogs received unencapsulated free islets as controls. Diabetes was confirmed by the absence of circulating C-peptide levels ($\leq 0.15$ pg/ml), abnormal intravenous glucose tolerance test (K-values 0.6±0.4), and elevated glycosylated hemoglobin (HbAlc) levels (7.3±1.4). All animals required daily insulin injections (1 to 4 U/kg) to maintain glucose control. Canine islets were prepared from pancreata of outbred donor dogs and transplanted intraperitoneally either as free islet controls (n=3) or as microencapsulated islets (n=6).

Figure 2:
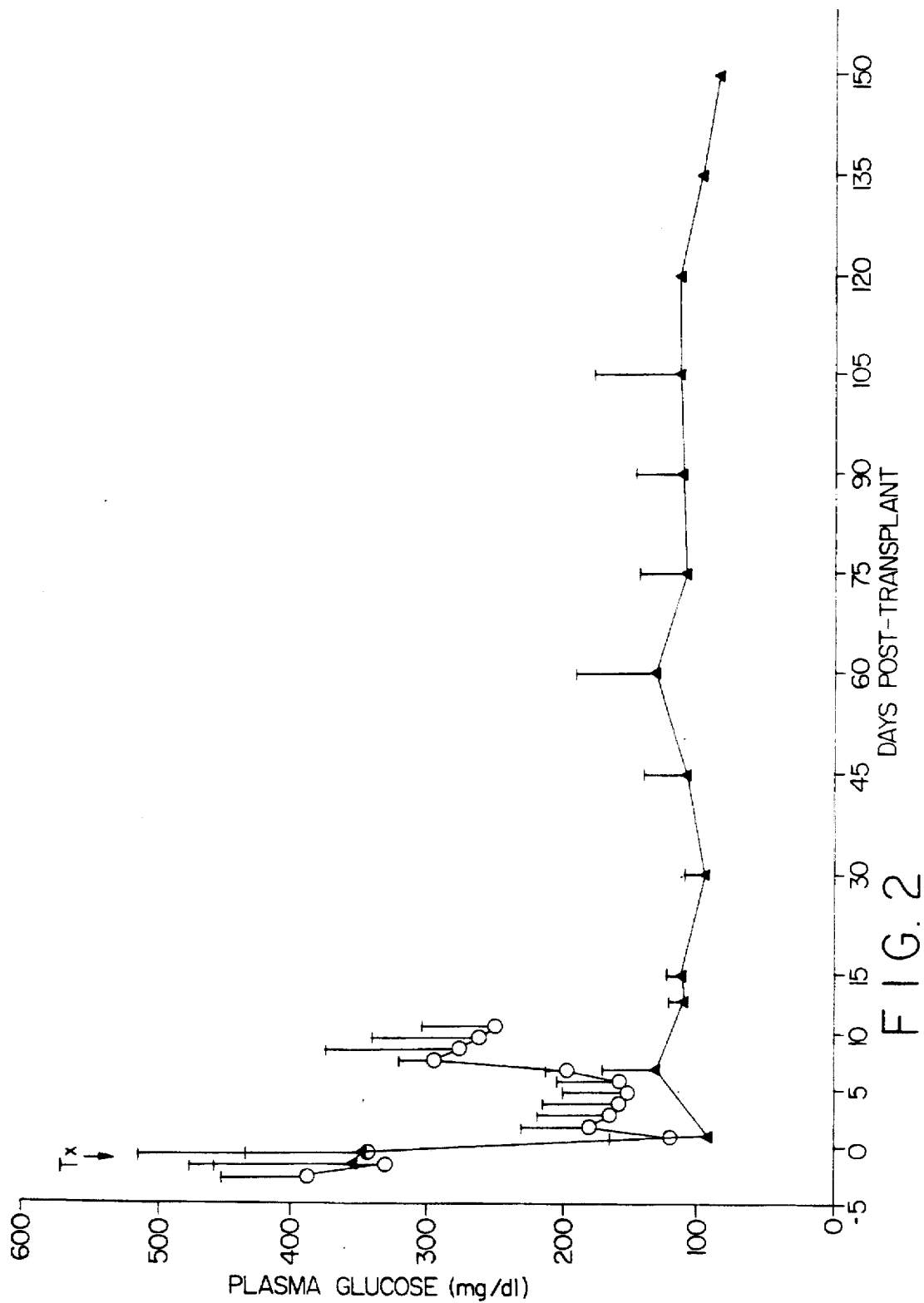
FIG. 2 illustrates the successful reversal of diabetes in the large animal model by islets encapsulated in compositions which passed the explosion, implosion and diffusion functional assays. The free islet transplant group is designated by ○, and the encapsulated islet test group is designated by ▲.

All 6 encapsulated islets recipients were rendered euglycemic within 24 hours of implantation, and remained free of insulin requirements for a median period of >100 days (see FIG. 2). In contrast, the recipients receiving unencapsulated islets rejected their grafts at 8 to 12 days.

Figure 3:
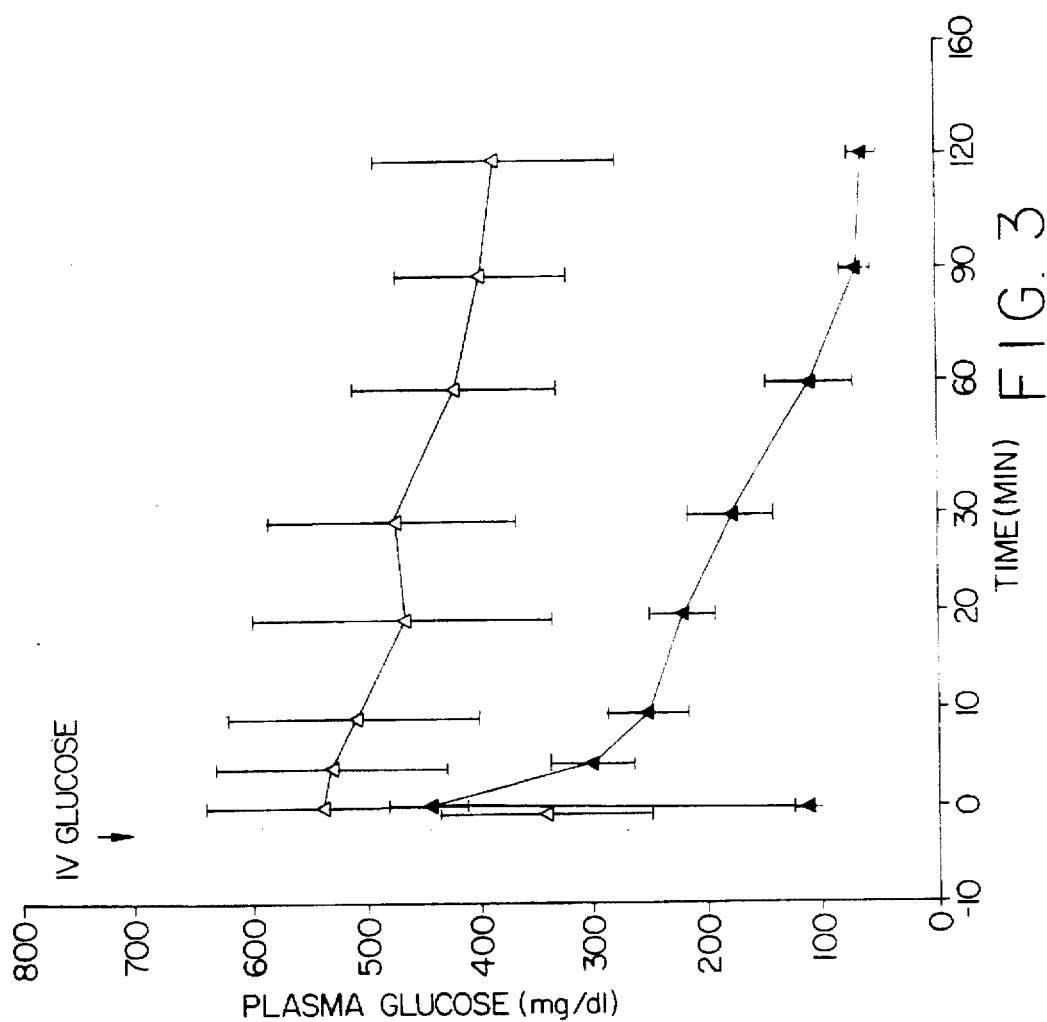
FIG. 3 presents the results of intravenous glucose tolerance test post transplantation, demonstrating normal diffusion of insulin in vivo from the encapsulated canine islets. Pre-transplant values (N=6; K value=0.6±0.4) are noted by Δ, and values 2 weeks post-transplant (N=6; K value= 2.6±0.8) are noted by ▲.

This is the first known report of successful long-term reversal of diabetes in the large mammalian species body by a single injection of microencapsulated islets. Glucose tolerance tests performed pre and 14 days post encapsulated islet transplant revealed a physiological release of insulin with normalization of blood glucose following a systemic injection of glucose (K-value=0.59±0.51 and 3.0±0.74 respectively (see FIG. 3)—thus demonstrating the adequate diffusion capacity of the intraperitoneal encapsulated islet. Evidence of long-term islet function (thereby demonstrating the stability of the capsule gel core and the immunoprotectivity of the capsule membrane), was provided by improvements in the recipients' body weight, as well as by parameters demonstrating improved metabolic control (e.g., improved glycosylated hemoglobin levels, improved cholesterol levels and improved K values). Immunohistochemical examination of the capsule retrieved 67, 90, 120 and 175 days post-transplant revealed capsules with intact membranes, intact gel cores and viable islets staining positive with anti-insulin antibodies. This is the first report of long term survival of encapsulated islets in the large animal models.

Figure 4:
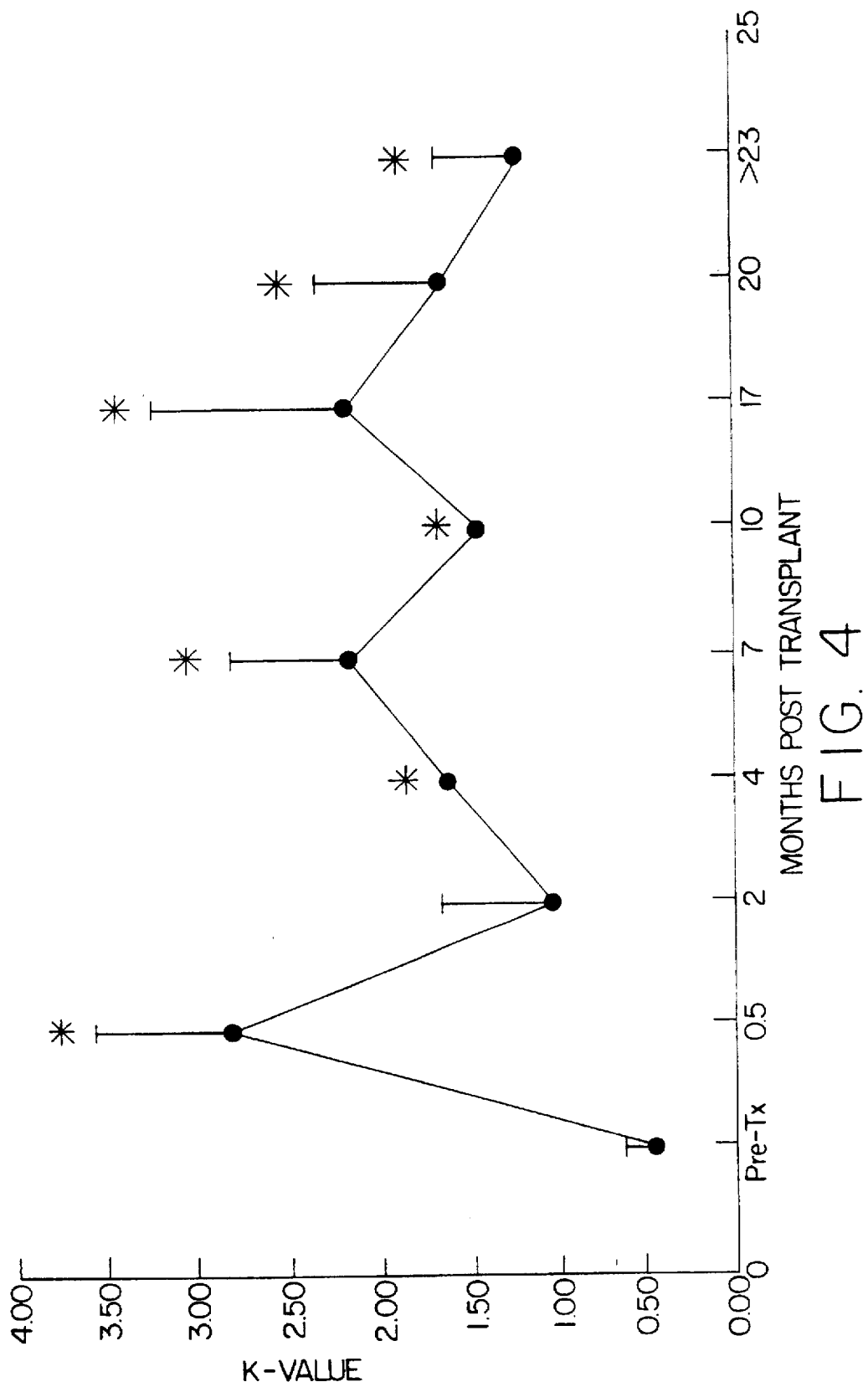
FIG. 4 presents the results of intravenous glucose tolerance testing (IVGTT), providing K-values pre- and post-transplant, demonstrating ongoing long-term islet survival. An * signifies that $p<0.05$, indicating that the K-values are significantly different from pre-transplant values.
Figure 5:
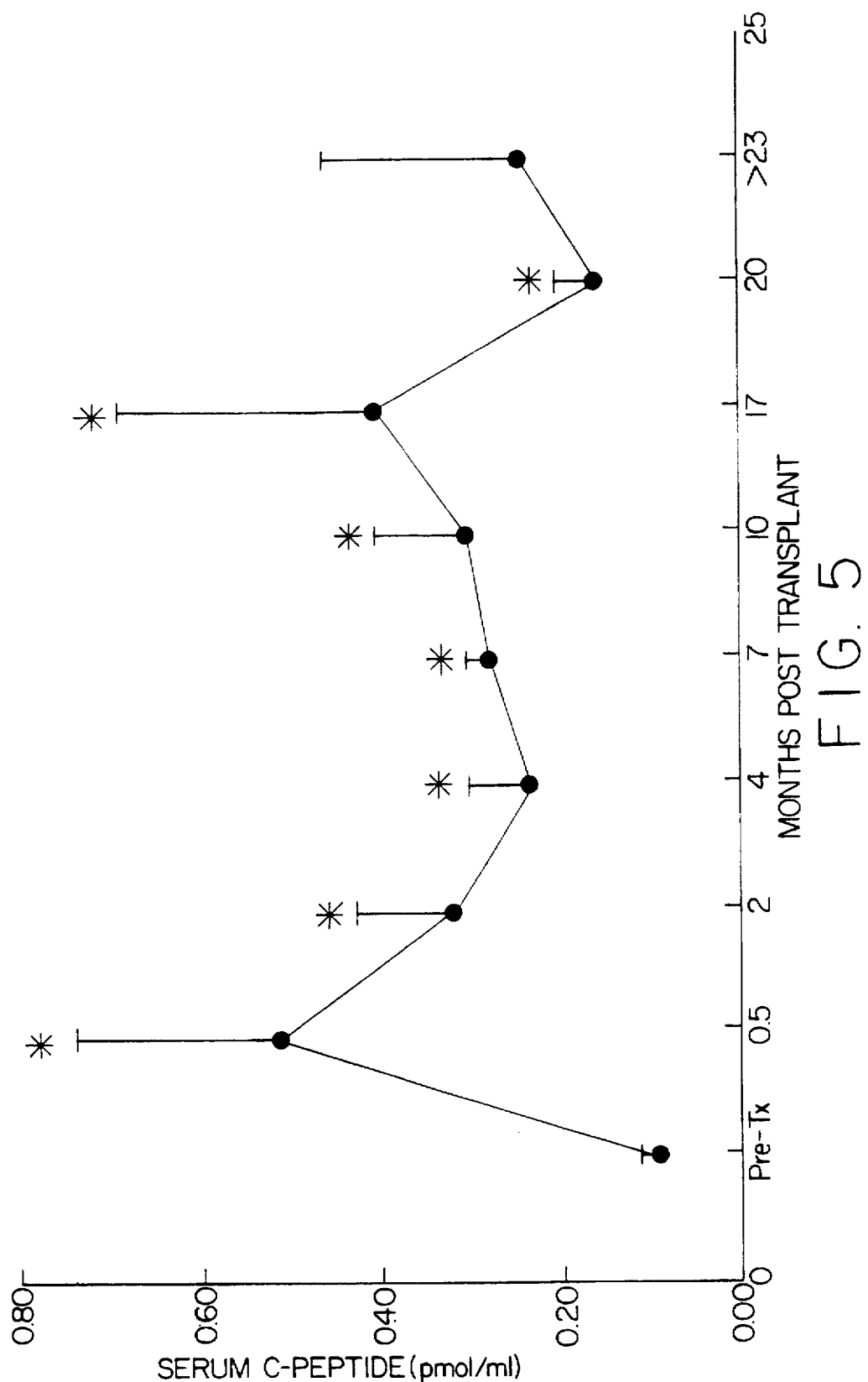
FIG. 5 summarizes basal C-peptide levels measured pre- and post-transplant, demonstrating ongoing long-term islet survival. An * signifies that $p<0.05$, indicating that the basal C-peptide levels are significantly different from pre-transplant values.
Figure 6:
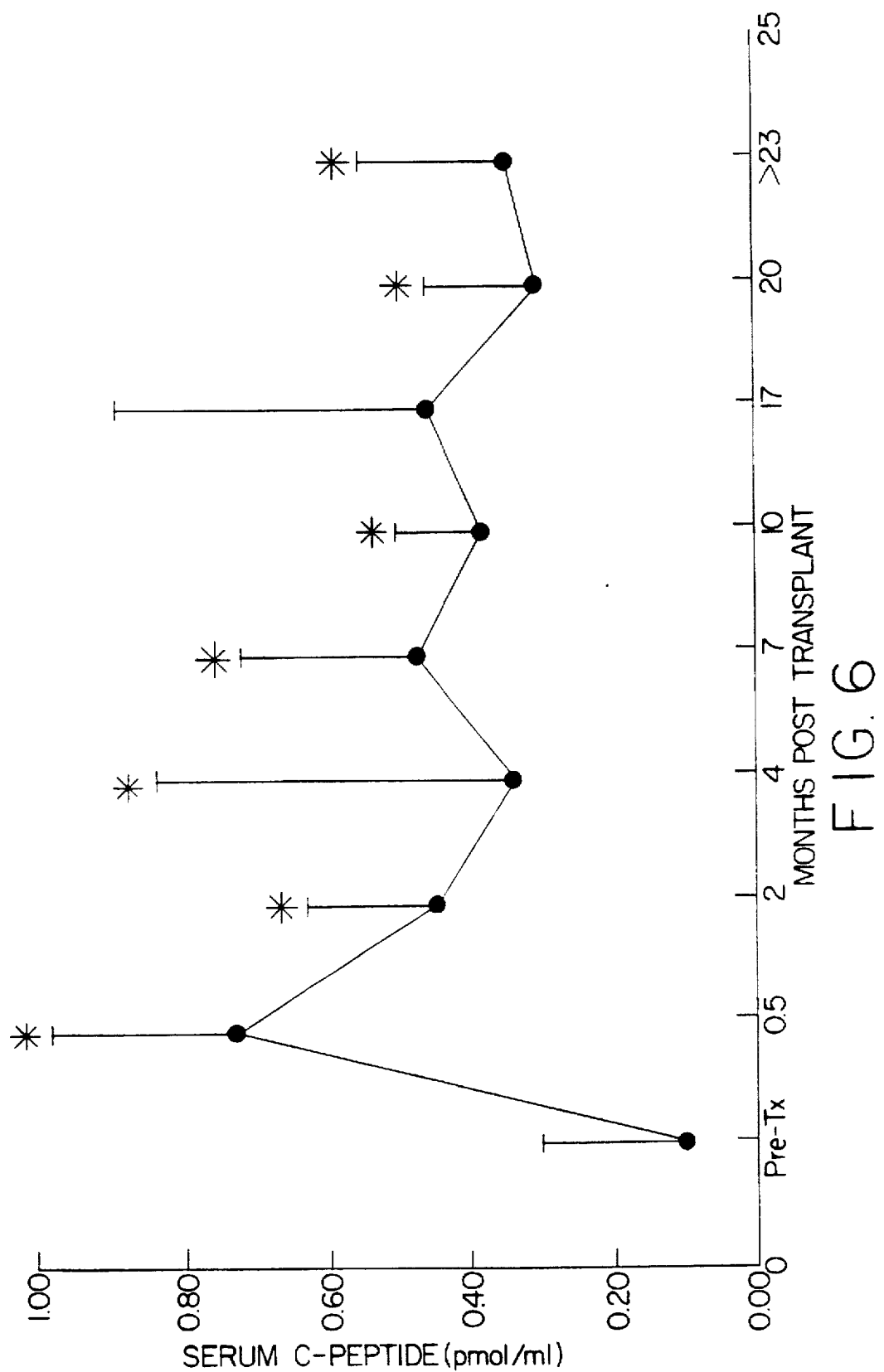
FIG. 6 summarizes peak C-peptide levels measured pre- and post-transplant, demonstrating ongoing long-term islet survival. An * signifies that p<0.05, indicating that the peak C-peptide levels are significantly different from pre-transplant values.
Figure 7:
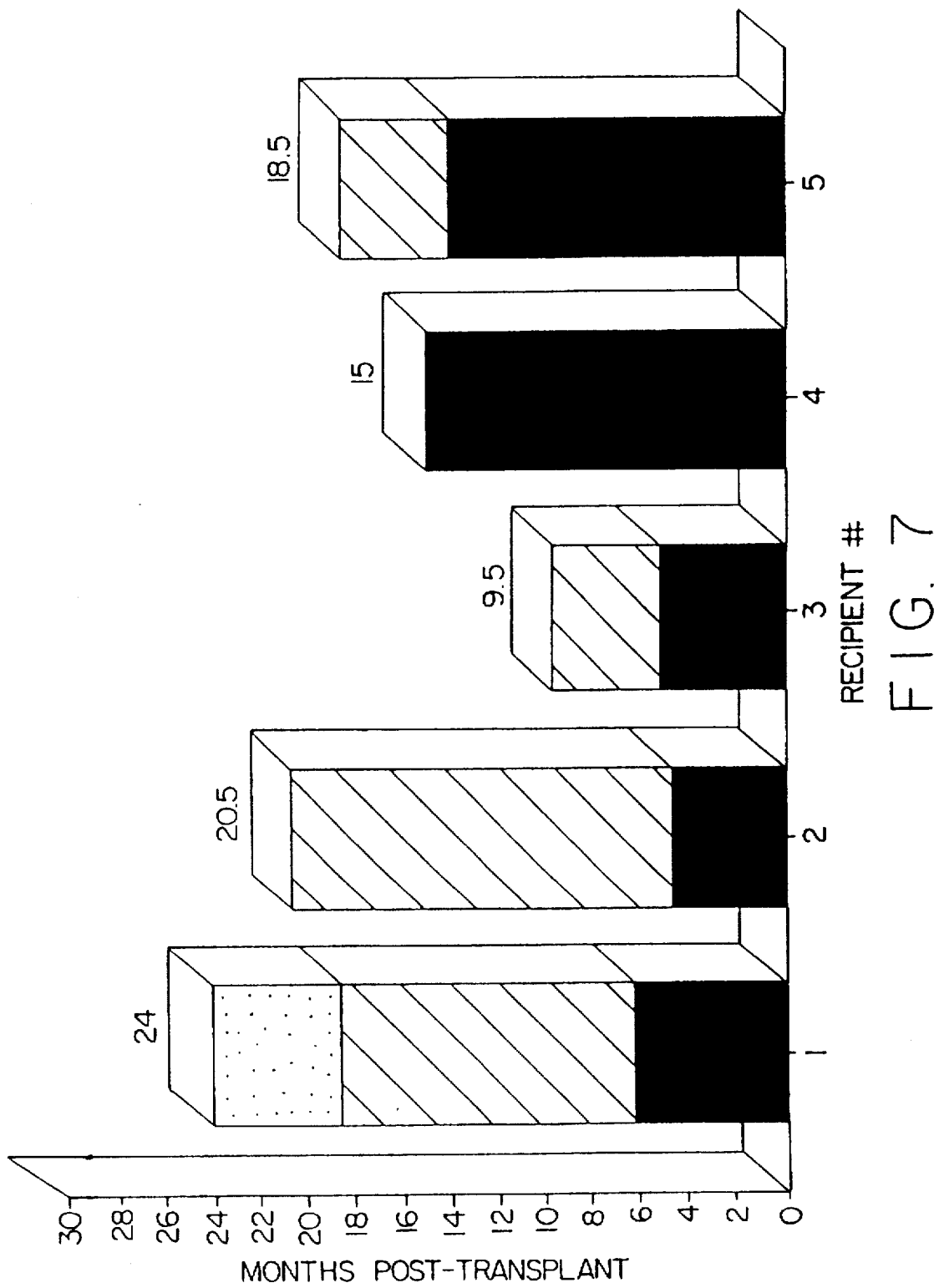
FIG. 7 summarizes the duration of ongoing islet survival in large animal models with islets encapsulated using novel capsules described herein. Black bars represent the results after a first transplant; diagonally striped bars represent results after a second transplant; and shaded bars represent results after a third transplant.

Following return to exogenous insulin therapy, 4 dogs received a second transplant, and one received a third implant of islets encapsulated in the formulations described above. Islet survival and ongoing function in these animals was demonstrated by significant improvement of metabolic control as evidenced by improved body weights, improved response to a systemic glucose challenge (K-values) (see FIG. 4), ongoing endogenous insulin secretion as evidenced by basal (see FIG. 5) and stimulated C-peptides (see FIG. 6). Based on these objective criteria, it is demonstrated for the first time that islets encapsulated in these novel formulations survive for as long as 732 days (see FIG. 7). There are no reports in the literature of this length of islet survival using intraperitoneal encapsulated islets in the large animal model. FIG. 7 demonstrates the duration of islet survival in these recipients receiving multiple implants and FIGS. 4, 5 and 6 demonstrate objective evidence of improved, ongoing metabolic control.

EXAMPLE 5

Capsule Formulations which Provide Long-Term Function in the Highly Discordant Xenograft Model The capsule formulations described above were used to encapsulate human and canine islets for transplantation into diabetic Lewis rats. All formulations passed the explosion, implosion and diffusion criteria as defined above. Diabetic Lewis rats were transplanted intraperitoneally with the following:

(i) empty capsule controls (n=4);

(ii) encapsulated canine islets (n=6)—discordant xenograft;

(iii) encapsulated human islets (n=6)—discordant xenograft; or (iv) untreated diabetic control (no transplant) n=4.

In the rats receiving encapsulated human and encapsulated canine islets, successful reversal of diabetes was achieved for >40 days in both groups with a short course (10-day) of cytokine suppression using cyclosporine. This was evidenced by normalization of serum glucose levels (<200mg %), reduction in daily urine volume and maintenance of the animals body weight. Furthermore, a glucose tolerance test performed in the rats receiving encapsulated canine and human islets showed normalization of the insulin response to a systemic glucose challenge, with K-values of 2.92±1.26 and 3.5±0.7, respectively. In contrast, the rats receiving empty capsules (controls) and the untreated diabetic rats (controls) demonstrated abnormal K-values in response to a systemic glucose challenge (K=0.6±0.12 and 0.4±0.15, respectively).

This is believed to be the first demonstration of long-term successful reversal of diabetes in a highly discordant xenograft (human/canine islets to rat). Anyone skilled in the art will recognize that these formulations could be applied to discordant xenografts in large mammalian species, e.g., pig islets to man.

Figure 8:
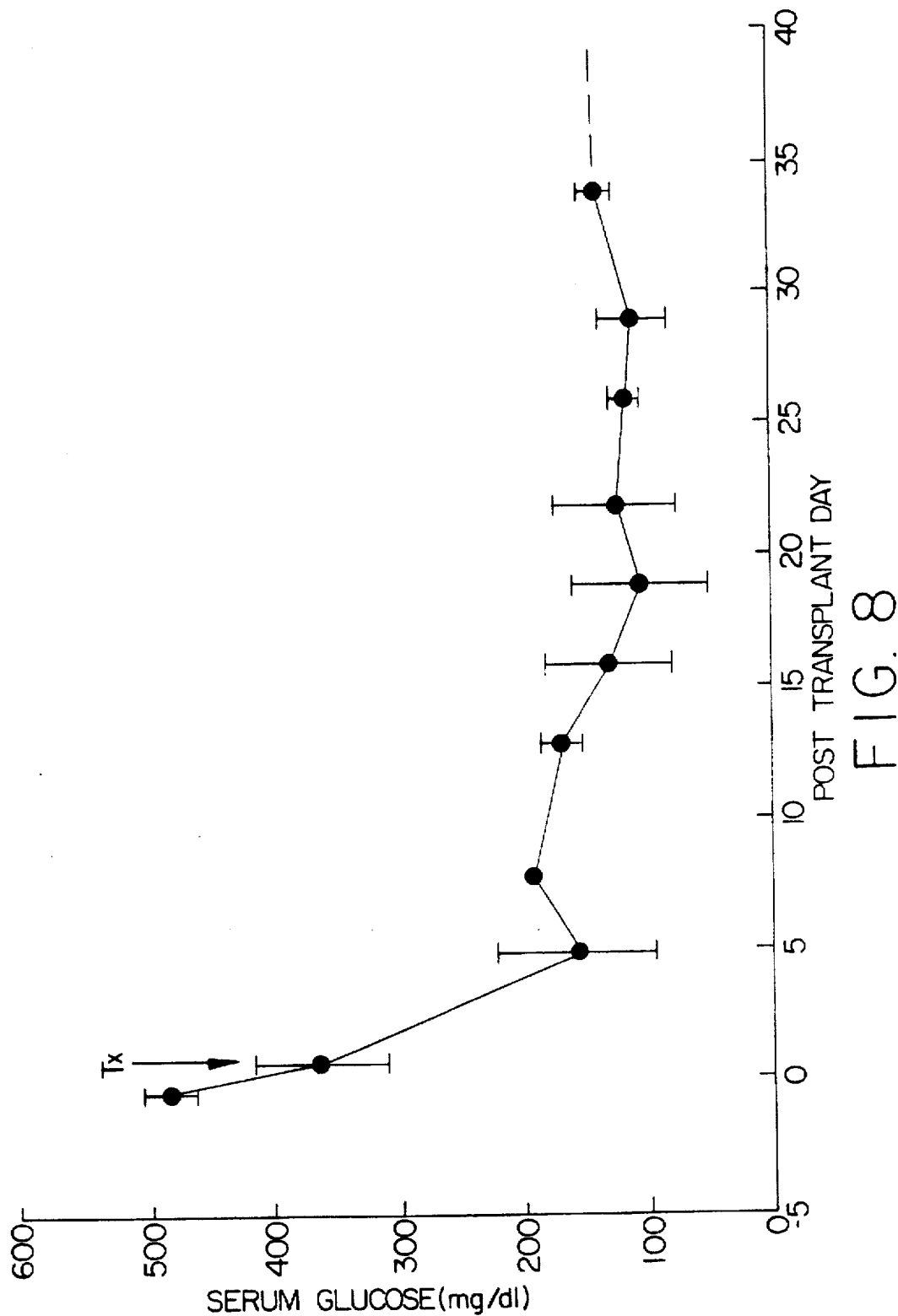
FIG. 8 presents serum glucose levels achieved with a discordant xenograft (dog to mouse, n=4), demonstrating successful xenograft transplantation using encapsulated canine islets in diabetic mice without immunosuppression.

A variation of the formulations described above has been explored in the macrocapsule form, i.e., microcapsules formulated by the methods described above can all be entrapped within a solid macrogel of alginate. This macrogel is formed as an inhomogeneous gel using 1.8% alginate in 1:50 $BaCl_2$:$CaCl_2$ ratio of 0.05M $CaCl_2$. FIG. 8 demonstrates successful reversal of diabetes in mice following transplantation of macroencapsulated retrievable canine islets. Serum glucose levels are normalized in all recipients without the use of immunosuppression in this highly discordant transplant model. This is the first report of long term reversal of diabetes by intraperitoneal implantation of encapsulated, retrievable islets in such a discordant xenograft.

Other Cell Types

It is clear to anyone skilled in the art that these formulations for in vivo transplantation can be applied to transplantation of any biologically active material or cell type, including live cells, adrenal cells, neural cells, any naturally occurring cell secreting a biologically active material, or any genetically engineered cell doing the same.

While the invention has been described in detail with reference to certain preferred embodiments thereof, it will be understood that modifications and variations are within the spirit and scope of that which is described and claimed.

That which is claimed is:

1. A method of determining whether a capsule will be stably functional for a long period in vivo, said method comprising testing said capsule to determine if it passes each of the following tests:

a) withstanding disruption following immersion in distilled water, wherein at least 5% of a population of capsules remain intact after 24 hours of immersion;

b) wrinkling on the membrane surface of said capsule is no greater than a grade 2+ in the implosion assay;

c) swelling no more than 180% of its original size after 12 hours immersion in 0.9% saline; and d) secreting end product at about basal levels or greater.

2. The method of claim 1 wherein said long period is greater than 30 days.

3. The method of claim 1 wherein said long period is greater than 100 days.

4. The method of claim 1 wherein at least 33% of a population of capsules remain intact after 24 hours of immersion in distilled water.

5. The method of claim 1 wherein at least 69% of a population of capsules remain intact after 24 hours of immersion in distilled water.

6. The method of claim 1 wherein at least 84% of a population of capsules remain intact after 24 hours of immersion in distilled water.

7. The method of claim 1 wherein wrinkling on the membrane surface of said capsule is no greater than a grade 1+ in the implosion assay.

8. The method of claim 1 wherein said capsule swells no more than 100% of its original size after 12 hours immersion in 0.9% saline.

9. The method of claim 1 wherein said capsule swells no more than 20% of its original size after 12 hours immersion in 0.9% saline.

10. The method of claim 1 wherein said capsule secretes end product at 1.5× basal levels or greater.

11. The method of claim 1 wherein said capsule secretes end product at 2× basal levels or greater.

12. A method of determining whether a capsule will be stably functional for at least 100 days in vivo, comprising testing said capsule to determine if it passes each of the following tests:

a) withstanding disruption following immersion in distilled water, wherein at least 84% of a population of capsules remain intact after 24 hours of immersion;

b) wrinkling on the membrane surface of said capsule is no greater than a grade 2+ in the implosion assay;

c) swelling no more than 20% of its original size after 12 hours immersion in 0.9% saline; and d) secreting end product at about 1.5× basal levels or greater.

* * * * *